United States Patent [19]

Scharf

[11] Patent Number: 4,867,763
[45] Date of Patent: Sep. 19, 1989

[54] PROCESS AND EQUIPMENT FOR THE FRACTIONAL DESUBLIMATION OF SOLIDS IN VAPOR FORM FROM GAS/VAPOR MIXTURES

[75] Inventor: Helmut Scharf, Schermbeck, Fed. Rep. of Germany

[73] Assignee: Huels Aktiengesellschaft, Marl, Fed. Rep. of Germany

[21] Appl. No.: 228,170

[22] Filed: Aug. 4, 1988

[30] Foreign Application Priority Data

Sep. 12, 1987 [DE] Fed. Rep. of Germany ....... 3730747

[51] Int. Cl.[4] .............................. B01D 7/02; F25J 5/00
[52] U.S. Cl. ........................................... 55/72; 55/82; 55/269; 62/12
[58] Field of Search ................. 55/72, 82, 269; 62/12

[56] References Cited

U.S. PATENT DOCUMENTS

| 2,755,887 | 7/1956 | Boatright | 55/82 |
|---|---|---|---|
| 3,406,012 | 10/1968 | Rahn | 55/72 X |
| 4,055,397 | 10/1977 | Van Heel | 55/82 X |
| 4,080,182 | 3/1978 | Vítovec et al. | 55/269 X |
| 4,135,893 | 1/1979 | Roberts | 55/82 |
| 4,181,508 | 1/1980 | Schmid et al. | 55/82 |
| 4,281,518 | 8/1981 | Müller et al. | 62/12 |
| 4,528,006 | 7/1985 | Vítovec et al. | 55/269 |
| 4,546,611 | 10/1985 | Eby et al. | 55/269 X |
| 4,725,291 | 2/1988 | Ueoka et al. | 55/82 |
| 4,773,923 | 9/1988 | Scharf | 55/82 X |

*Primary Examiner*—Robert Spitzer
*Attorney, Agent, or Firm*—Oblon, Spivak, McClelland, Maier & Neustadt

[57] ABSTRACT

Solids are fractionally desublimed in vapor form from a gas/vapor mixture by providing a nozzle through which a gas/vapor mixture containing a solid is accelerated, the nozzle being provided with a concentric opening which allows a cooling gas flowing laterally at a high velocity to impinge upon and mix with the gas/vapor mixture flowing through the nozzle in the mixing zone of the nozzle thereby forming a gas/solid mixture, passing the gas/vapor mixture through the nozzle and the cooling gas through the concentric opening such that the angle at which the cooling gas emerges from the concentric opening into the flow of the gas/vapor mixture to the direction of flow of the gas/vapor mixture ranges from 0.17 pi rad to 0.75 pi rad, the temperature of the resulting gas/solid mixture in the mixing zone being adjusted by the flow rate of the cooling gas in such a way that the temperature is below the sublimation temperature of the desired product solid but above the sublimation temperature of the by-products in the gas/vapor mixture, and allowing the gas/solid mixture to exit the nozzle in the direction of flow of the gas/vapor mixture through the nozzle.

19 Claims, 1 Drawing Sheet

PROCESS AND EQUIPMENT FOR THE FRACTIONAL DESUBLIMATION OF SOLIDS IN VAPOR FORM FROM GAS/VAPOR MIXTURES

BACKGROUND OF THE INVENTION

1. Field of the Invention:

The invention relates to a process of fractionally desublimating solids in vapor form.

2. Description of the Background:

The invention has the purpose of making the desublimation of solids in vapor form from gas/vapor mixtures by means of cooling gases simpler and less prone to faults.

Desublimation is the physical process in which there is a direct transition of a solid in the vapor state form to the solid form.

A number of inorganic and organic solids are prepared by initially forming the solid as a vapor in a carrier gas and then fractionally desubliming by cooling of the gas/vapor mixture. This fractional desublimation can be accomplished by cooling the gas/vapor mixture on temperature-controlled wall surfaces, the equipment frequently being provided with mechanical scraping devices. Another possibility of desubliming solids from the gas phase involves direct cooling of the gas/vapor mixture by means of coolants which are gaseous under the desublimation conditions. In the process of British Pat. No. 1,081,579, for example, water, as a preferred coolant, is injected under pressure into the gas/vapor mixture and vaporized. In this process, however, a part of the solid by-products is also precipitated, in addition to the solid main product, on the water droplets before the latter have been fully vaporized, so that fractional desublimation is hardly possible. Because of the preferred use of water, the process is also unsuitable in cases where water-sensitive substances such as, for example, acid anhydrides are to be desublimed. Since the walls of the desublimator are heated and the residence time of the gas/vapor coolant mixture in the desublimation zone is very long, a part of the coolant is additionally heated by the walls, so that large quantities of coolant are required. This applies very particularly when cooling gases are used, with which the high latent heat of vaporization of water is not available for cooling. Cooling gas is additionally also introduced at the bottom of the desublimator. As a result, the total quantity of coolant required, and hence also the quantity of exit gas, are further increased.

Another process is described in German Pat. No. 1,108,663. Here, the carrier gas, already freed from product, is circulated through coolers and mixed with the product-carrying gas. At the same time, liquid product is injected into the mixing chamber. Fractional desublimation is hardly feasible by this process.

French Specification No. 2,082,822 shows a method in which desublimation is performed with air in two series-connected pipes, in order to achieve better precipitation of the solid on the pipe walls and to obtain a purer solid. This process requires large wall areas which cannot be realized industrially, and the pipes are rapidly blocked by the precipitated solid.

In a similar process, the cooling of the gas/vapor mixture is carried out by means of cooling gases and with the use of additionally cooled pipes provided with scraping devices, as described in German Patent Specification No. 2,617,595. In this expensive process which is prone to faults, the highly disperse part of the product stream is circulated. Fractional desublimation is again impossible.

Yet another desublimation process is described in German Patent Specification No. 1,544,129, in which the carrier gas containing the solid in vapor form and the cooling gas form two coaxial gas cylinders which rotate in the same direction and move axially in opposite directions, and in which the sublimed solid is discharged from the desublimator with a part of the cooling gas. In this process, a very large quantity of cooling gas must be used in order to prevent the gas/vapor mixture from coming into contact with the wall, and in order to discharge the desublimed solid. In this process, too, fractional desublimation is not possible.

In German Offenlegungsschrift No. 3,501,371.0, the fractional desublimation of solids in vapor form from a gas/vapor mixture is accomplished by means of a cooling gas, in such a way that the gas/vapor mixture, accelerated by means of a nozzle, and the cooling gas, likewise accelerated by means of a nozzle, impinge on each other at very high flow velocities, the nozzles being located opposite one another and the nozzle axes lying on a straight line. In this process, depositions of material on the nozzles or blockages of the nozzles with material can take place, if wide irregularities occur in the feed of the gas/vapor mixture or of the cooling gas. If, for example, the feed of the gas/vapor mixture is briefly interrupted or very greatly reduced, the cold cooling gas can strike the nozzle of the gas/vapor mixture and cool the latter to some extent, so that the solid which is to be desublimed can in part already precipitate on the nozzle orifice and effect a deflection of gas/vapor mixture. Since the two gas streams then no longer impinge frontally on one another, retarded and incomplete mixing of the two gas streams is likely to occur, so that a more impure product is obtained. The same can also happen when, conversely, cooling gas is fed improperly, the result of which is that the gas/vapor mixture strikes the cold cooling gas nozzle and the solid, which is to be desublimed, precipitates partially on the cold cooling gas nozzle. A need therefore continues to exist for an improved technique of fractionally desubliming solids.

SUMMARY OF THE INVENTION

Accordingly, one object of the present invention is to provide a process and apparatus for fractionally desubliming solids from gas/vapor mixtures by direct cooling of the gas/vapor mixture by means of a cooling gas.

Another object of the present invention is to provide a nozzle for fractionally desubliming solids in which cooling gas and gas/vapor mixture are mixed at high acceleration in such a fashion that deflection of the gas streams because of deposition of small quantities of product in the nozzle is no longer possible.

Briefly, these objects and other objects of the present invention as hereinafter will become readily apparent can be attained by a process in vapor form from a gas/vapor mixture comprising providing a nozzle through which a gas/vapor mixture containing a solid to be desublimed is accelerated, said nozzle provided with a concentric opening which allows a cooling gas flowing laterally at a high velocity to impinge upon and mix with the gas/vapor mixture flowing through said nozzle in the mixing zone of said nozzle thereby forming a gas/solid mixture, passing said gas/vapor mixture through said nozzle and said cooling gas through said concentric opening such that the angle at which the cooling gas emerges from the concentric opening into the flow of gas/vapor mixture to the direction of flow of the gas/vapor mixture ranges from 0.17 pi rad to 0.75 pi rad, the temperature of the resulting gas/solid mixture in the mixing zone being adjusted by the flow rate of the cooling gas in such a way that the temperature is below the sublimation temperature of the desired product solid but above the sublimation temperature of the by-products in said gas/vapor mixture, and allowing the gas/solid mixture to exit said nozzle in the direction of flow of the gas/vapor mixture through the nozzle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
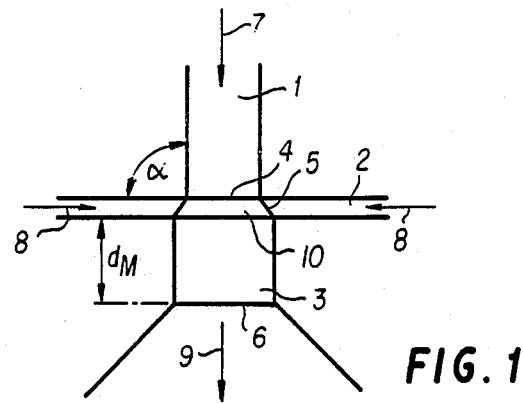
FIG. 1 is a diagram of the desublimation nozzle of the present invention.

Referring to FIG. 1, the gas/vapor mixture, from which a solid is to be desublimed, is accelerated by nozzle 1 flowing in direction 7 to velocities of between 10 and 200 m/second, preferably 20 to 150 m/second. Flow velocities below 10 m/second are also possible, but a less pure solid is obtained at low velocities, the degree of contamination of the solid also depending on the difference between the desublimation temperatures of the main product and the by-products. Preferably, the flow velocities are greater than 10 m/second and, in the case of solids, where the desublimation temperatures of the main product and of the by-products are very close to one another, such as is the case of, for example, pyromellitic dianhydride, flow velocities of the gas/vapor mixture of more than 30 m/second are preferred. Even though the desubliming solid becomes cleaner with increasing flow velocity and hence decreasing cooling time, there is a technically relevant upper limit, since the desubliming solid particles become increasingly smaller with increasing flow velocity and must be separated from the gas stream by means of finer filters. A further point is that, at very high flow velocities upstream of the nozzle, correspondingly high pressures must be built up, which involve additional costs. Flow velocities of the gas/vapor mixture of less than about 200 m/second are therefore regarded as technically feasible, velocities of less than 100 m/second being preferred.

The cooling gas flowing in direction 8 is likewise accelerated by the concentric opening 2 to velocities of between 10 and 200 m/second, preferably 30 to 100 m/second. Mixing of the cooling gas with the gas/vapor mixture takes place in mixing zone 10. The resulting gas/solid mixture leaves mixing zone 10 through outlet 3 flowing in direction 9. The symbol $d_M$ denotes the length of the lower part of the mixing zone 10, while the symbol $\alpha$ is the angle between the direction of flow of the cooling gas and the direction of flow of the gas/vapor mixture.

Substances which are in the form of gas or vapor under the desublimation conditions and which do not react with the solid which is to be precipitated, can be used as the cooling gas for the process of the present invention. Suitable gases and vapors include nitrogen, oxygen, carbon dioxide, carbon monoxide and mixtures of these gases. Air is particularly preferred as the cooling gas. The temperature of the cooling gases should be as low as possible, since the required rate of cooling gas flow is lower, the lower the temperature of the gas. Gases at room temperature are preferred. However, gases at a higher temperature such as air which has been heated by the required compression step, can also be used, but in this case the consumption of air is correspondingly higher.

An aspect of the invention is the equipment designed for the fractional desublimation of solids in vapor form from a gas/vapor mixture by means of a cooling gas. An important part of the apparatus is the nozzle through which the gas/vapor mixture passes. The nozzle contains a concentric opening which surrounds the path through which the gas/vapor flows, and it is the opening through which the cooling gas flows to mix with the gas/vapor mixture. The nozzle for the gas/vapor mixture is round, polygonal or slot-shaped, and the diameter or the diagonal or the slot width of this nozzle is 2 to 12 mm, preferably 4 to 8 mm. The shape of the orifice at the opening for the cooling gas is adapted to the shape of the nozzle orifice for the gas/vapor mixture.

The nozzle orifice for the cooling gas and the housing consist of a heat-insulating material which is stable at the temperatures employed, such as, for example, heat-resistant plastics or glass ceramics. Polyimides, polyamide-imides, polyethers and Teflon, as well as Teflon-like plastics are preferred, and the materials may be mechanically stabilized by additives. If Teflon is used, it is advantageous to surround the desublimation equipment, which mechanically supports the Teflon, with a shell of ceramic material or with a metal shell, the temperature of which can be controlled from the outside.

The nozzle for the gas/vapor mixture consists as a rule of a material of high thermal conductivity, such as, for example, copper, silver or gold. Copper or silver-plated copper is preferred. However, it is also possible to use a material of lower thermal conductivity, such as, for example, VA stainless steel, if the nozzle is heated. The heater can be fitted in the metal body or on the outside of the metal body.

The nozzle orifice for the gas/vapor mixture can be circular, elliptical, polygonal or slot-shaped; a circular orifice is preferred in the case of low gas rates, and a slot-shaped orifice is preferred in the case of high gas rates. The size of the nozzle orifice depends on the desired gas throughput and on the desired flow velocity. As a rule, the diameter or the diagonal or the slot width is 2 to 12 mm, preferably 4 to 8 mm. Although nozzles of a diameter smaller than 2 mm are possible, they have no technical advantages. The diameter or the slot width has no fixed upper limit and, instead, the latter depends on the throughput of gas/vapor mixture and on the difference between the desublimation temperatures of the product and byproducts, and on the required purity of the product. Since, at the same flow velocity, the gas rates increase with the square of the radius of the nozzles, mixing of the two individual streams decreases with increasing rates of the gas/vapor mixture and cooling gas and, consequently, the purity of the product decreases.

The length of the nozzle for the gas/vapor mixture (length of the pipe of reduced cross-section) is not important for the process. Since, however, the flow resistance increases with increasing length of the nozzle, the nozzle should not be too long. On the other hand, it must also not be too short, since the distance between the space containing the gas/vapor mixture and the space, in which the cooling gas flows, should be as large as possible, in order to obtain the smallest possible heat flux from the gas/vapor mixture to the cooling gas. A length of 30 to 50 mm is very suitable.

The orifice 5 of the nozzle for the cooling gas is an annular gap, the shape and size of which depend on the orifice of the nozzle for the gas/vapor mixture, since one edge of the nozzle for the cooling gas is at the same time the inner periphery of the orifice of the nozzle for the gas/vapor mixture (contact line between 5 and 4 in FIG. 1).

The geometrical shape of the nozzle outlet for the cooling gas can accordingly be the shell of a circular cylinder, an inclined cylinder, a circular truncated cone, an inclined truncated cone, a pism with polygons as the base area and truncated pyramids with polygons as the base area. In the simplest case of a circular cylinder, for example, the gap width of the nozzle (height of the cylinder) for the cooling gas is one quarter of the diameter of the nozzle for the gas/vapor mixture, if the rates of gas/vapor mixture and cooling gas and the velocities of the two gas streams are to be the same. In the case of a slot-shaped nozzle for the gas/vapor mixture, having the length L and the width B, the height h of the slot for the cooling gas is, under the same conditions:

$$h = \frac{B \times L}{2(B + L)}.$$

Apart from the flow rates of gas/vapor mixture and cooling gas and their temperatures, the velocity of the gas/solid mixture formed from the gas/vapor mixture and the cooling gas also depends on the cross-section 6 of the orifice at the outlet from the mixing zone. This cross-section is chosen such that the velocity of the gas/solid mixture is between 10 and 200 m/second. Higher velocities do not have any technical advantages, and lower velocities lead, because of the less favorable geometry which is then necessary, to premature deflection of the cooling gas stream in the direction of the outlet, so that a poorer product is obtained. Preferably, the cross-section at the outlet of the mixing zone is chosen such that the velocity of the gas/solid mixture is of the order of magnitude of the velocities of the gas/vapor mixture in the cooling gas.

If appropriate, the orifice at the outlet from the mixing zone can be formed by an orifice plate.

The length $d_M$ of the lower part of the mixing zone 3 should be as short as possible. Lengths of less than 12 mm have proved suitable. In the case of lengths greater than 15 mm, product can deposit on the wall. The wall can be provided with slot-shaped recesses, in order to reduce the heat flux in the direction of the cooling gas. The shape of the nozzle outlet is not a critical part of the invention. For example, it can have the shape of a cone or it can be a Laval nozzle. The wall of the nozzle outlet can be heated from the outside, if necessary.

The process according to the invention has the advantage that it is very simple and allows a clean separation of the solid from the likewise desublimable by-products, so that a very pure solid is obtained in virtually quantitative yield. Short-term fluctuations in the feed of the gas/vapor mixture or of the cooling gas do not lead to blockages of the nozzle. A further advantage is that the equipment according to the invention is also very simple, does not contain any mechanically moving parts and does not require any temperature-controlled wall surfaces. As a result of the simplicity of the process and the equipment, trouble-free running of the unit is possible, and the cost is low.

In the process of the above described German Offenlegungsschrift 3,501,371.0, rapid and uniform mixing of the two gas streams is carried out in a wall-free mixing zone, in order to avoid depositions of product on walls. In the investigation leading to the present invention, it was surprising to find that mixing of the two gas streams can also be carried out in the presence of walls, if the cooling gas impinges laterally and concentrically through an annular nozzle upon the gas/vapor mixture and rapid mixing of the two gas streams takes place as a result of high flow velocities of the two gas streams.

The following is believed to occur in the nozzle shown in FIG. 1. The gas/vapor mixture flows in the direction 7 through the nozzle orifice 4 into the mixing zone 10. The cooling gas emerging through the nozzle orifice 5 in the direction 8 impinges at the angle alpha upon the gas/vapor mixture and is mixed with the latter in the mixing zone 10. The resulting gas/solid mixture with the desublimed solid leaves the mixing zone through the orifice 6 in the direction 9 and passes to a device, which is not shown which filters out the sublimed solid from the gas.

Figure 2:
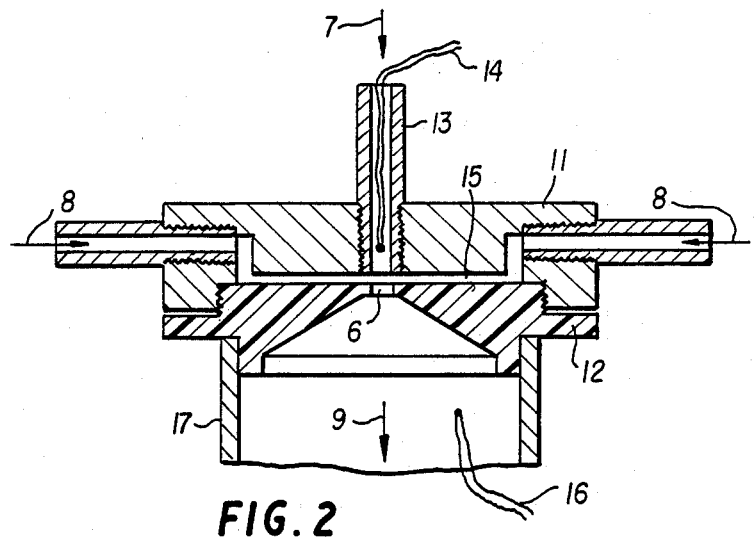
FIGS. 2 and 3 are diagrams of embodiments of the desublimation apparatus of the present invention containing the nozzle of the invention.
Figure 3:
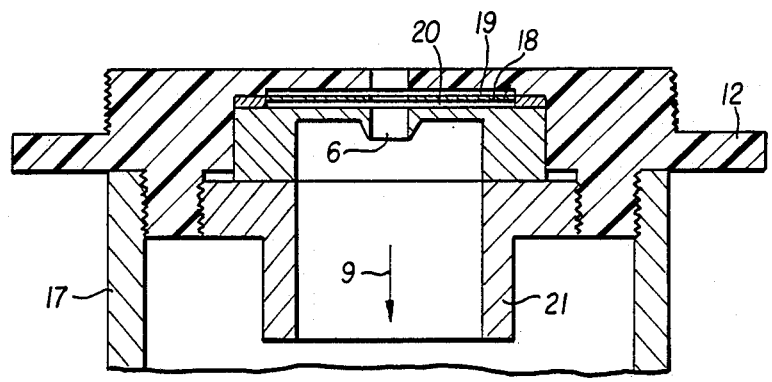

FIGS. 2 and 3 show two illustrative non-limiting embodiments of the equipment of the invention.

In the desublimation apparatus of the present invention, components 11 and 12 consist of reinforced polyimide. The nozzle 13 is a copper pipe and houses thermocouple 14. The gap 15 is the annular gap for the cooling gas. The thermocouple 16 is fitted underneath the nozzle.

Using the apparatus of the present invention, the present process is carried out as follows. The gas/vapor mixture flows in the direction 7 through the nozzle 13, wherein it is accelerated to the desired velocity. The temperature of the gas/vapor mixture is measured by the thermocouple 14. The cooling gas flows in the direction 8 through the gap 15, in which it is accelerated to the desired velocity. Above the orifice 6 of the mixing zone, the cooling gas impinges under an angle of 0.5 pi rad upon the gas/vapor mixture. The gas/vapor mixture is cooled there and the solid is desublimed. The resulting gas/solid mixture with the desublimed solid leaves the mixing zone through the orifice 6 in direction 9. The temperature of the gas/solid mixture is measured by the thermocouple 16. The cooling gas feed rate fed is controlled to maintain a constant cooling gas temperature or the cooling gas temperature is controlled at constant cooling gas rate. If desired, the housing 17 can be temperature-controlled. The gas/solid mixture is passed to a filter device, which is not shown and in which the desublimed solid is filtered out of the gas.

Another embodiment of the lower part 12 of the nozzle illustrated in FIG. 2 is shown in FIG. 3. By means of the additionally fitted plate 18, the two disc-shaped air chambers 19 and 20 are formed. The heat transport via the wall from the gas/solid mixture to the cooling gas is made more difficult by these two chambers; therefore, the temperature of the material located underneath the air chamber 20 is virtually the same as the temperature of the gas/solid mixture. Underneath the orifice 6 a cylindrical space is formed by the ring 21. The result is that the flow of the gas/solid mixture emerging from the orifice 6 is extended before the gas/solid mixture comes into contact with the temperature-controlled housing 17.

Having generally described this invention, a further understanding can be obtained by reference to certain specific examples which are provided herein for purposes of illustration only and are not intended to be limiting unless otherwise specified.

A gas/vapor mixture containing pyromellitic dianhydride (PMDA) was produced by oxidation of tetraalkylbenzenes with air. In addition to PMDA, the gas/vapor mixture contained as by-products, from which the PMDA had to be separated, trimellitic anhydride, methylisopropylphthalic anhydride, dimethylphthalic anhydride and a number of other compounds which were present only in small quantities and only some of which have been identified, such as aldehydes and quinones. The main quantity of the gas/vapor mixture consisted of nitrogen and oxygen and small quantities of water vapor, carbon monoxide and carbon dioxide. This gas/vapor mixture was first cooled by means of a heat exchanger to 230° C. and then, in desublimation equipment according to the invention, which consisted of the upper part 11 of the equipment illustrated in FIG. 2 and of the lower part 12 illustrated in FIG. 3, the mixture was accelerated in the nozzle 13 to about 29, 62 and 80 m/second and quenched with air at 25° C., which air was accelerated in the annular gap 15 to about 30, 60 and 80 m/second. The exact air rate was adjusted in light of temperature data provided by thermocouple 16 such that more than 99% of the PMDa present in the vapor phase were desublimed. The PMDA was separated from the gas phase by means of a filter and, after esterification, examined by gas chromatography. The purity was greater than 99% in all cases.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for fractionally desubliming solids in vapor form from a gas/vapor mixture, comprising:
   providing a nozzle through which a gas/vapor mixture containing a solid to be desublimed is accelerated, said nozzle provided with a concentric opening which allows a cooling gas flowing laterally at a high velocity to impinge upon and mix with the gas/vapor mixture flowing through said nozzle in the mixing zone of said nozzle, thereby forming a gas/solid mixture;
   passing said gas/vapor mixture through said nozzle and said cooling gas through said concentric opening such that the angle at which the cooling gas emerges from the concentric opening into the flow of gas/vapor mixture to the direction of flow of the gas/vapor mixture ranges from 0.17 pi rad to 0.75 pi rad, the temperature of the resulting gas/solid mixture in the mixing zone being adjusted by the flow rate of the cooling gas in such a way that the temperature is below the sublimation temperature of the desired product solid but above the sublimation temperature of the byproducts in said gas/vapor mixture; and
   allowing the gas solid mixture to exit said nozzle in the direction of flow of the gas/vapor mixture through the nozzle.

2. The process according to claim 1, wherein the flow velocities of the gas/vapor mixture and of the cooling gas are 10 to 200 m/second.

3. The process according to claim 2, wherein the flow velocities range from 20 to 150 m/second.

4. The process according to claim 1, wherein said angle between the direction in which the cooling gas emerges from the concentric opening and the direction of flow of the gas/vapor mixture is 0.5 pi rad.

5. The process according to claim 1, wherein said cooling gas is oxygen, nitrogen, carbon monoxide, carbon dioxide or mixtures thereof.

6. The process according to claim 1, wherein air is the cooling gas.

7. The process according to claim 1, wherein the flow velocity of said gas/solid mixture is 10 to 200 m/second.

8. The process according to claim 1, wherein the solid which is to be desublimed is a pyromellitic dianhydride.

9. An apparatus for fractionally desubliming solids in separate form from a gas/vapor mixture, comprising:
   a nozzle means progressively having a gas/vapor mixture inlet, a mixing zone having an interior surface, said gas/vapor mixture inlet having an orifice at the point in the nozzle where the gas/vapor mixture inlet joins the mixing zone, and a gas/solid mixture outlet, and
   a concentric opening in said nozzle which permits inflow of a cooling gas laterally into the nozzle where the cooling gas impinges upon and mixes with said gas/vapor mixture in said mixing zone at said orifice, said concentric opening for the cooling gas being of variable geometry whose shape corresponds to the shape of said orifice.

10. The apparatus of claim 9, wherein the nozzle orifice is round of a diameter ranging from 2 to 12 mm.

11. The apparatus of claim 9, wherein the nozzle orifice is polygonal having a diagonal of 2 to 12 mm.

12. The apparatus of claim 9, wherein the nozzle orifice is slot-shaped having a slot width of 2 to 12 mm.

13. The apparatus of claim 9, wherein the dimensions of the mixing zone are exactly the same as the corresponding dimensions of the nozzle orifice for the gas/vapor mixture or are greater than these dimensions.

14. The apparatus of claim 13, wherein the mixing zone is further confined by an orifice plate which itself has an orifice, the shape of which plate corresponds to the shape of the nozzle for the gas/vapor mixture, with the orifice of the orifice plate being located opposite the orifice for the gas/vapor mixture.

15. The apparatus of claim 14, wherein said orifice plate consists of a heat resistant, dimensionally stable and heat-insulating material.

16. The apparatus of claim 9, wherein the opening for the cooling gas and the interior surface of the mixing zone consist of a heat-resistant, dimensionally stable and heat-insulating material.

17. The apparatus of claim 9, wherein the nozzle for the gas/vapor mixture consists of a material of high thermal conductivity.

18. The apparatus of claim 9, wherein the nozzle for the gas/vapor mixture is heated.

19. The apparatus of claim 9, wherein for high flow rates of gas/vapor mixture and cooling gas, a correspondingly large number of nozzle orifices for the gas/vapor mixture and openings for the cooling gas are provided in a compound arrangement and the resulting streams of gas/solid mixtures flow at said gas/solid outlets into a common chamber.

* * * * *